(12) United States Patent
Blomqvist et al.

(10) Patent No.: US 8,630,700 B2
(45) Date of Patent: Jan. 14, 2014

(54) IMPLANTABLE HEART MONITORING DEVICE, SYSTEM AND METHOD

(75) Inventors: Andreas Blomqvist, Spånga (SE); Nils Holmstöm, Järfälla (SE); Sven-Erik Hedberg, Kungsängen (SE); Malin Öhlander, Stockholm (SE)

(73) Assignee: St. Jude Medical, AB, Jarfalla (SE)

( * ) Notice: Subject to any disclaimer, the term of this patent is extended or adjusted under 35 U.S.C. 154(b) by 463 days.

(21) Appl. No.: 12/808,041

(22) PCT Filed: Dec. 19, 2007

(86) PCT No.: PCT/SE2007/001134
§ 371 (c)(1),
(2), (4) Date: Jun. 14, 2010

(87) PCT Pub. No.: WO2009/078758
PCT Pub. Date: Jun. 25, 2009

(65) Prior Publication Data
US 2010/0268102 A1     Oct. 21, 2010

(51) Int. Cl.
*A61B 5/053*     (2006.01)

(52) U.S. Cl.
USPC .......................................... 600/513; 600/547

(58) Field of Classification Search
USPC .................. 600/506, 512, 513, 547; 607/24
See application file for complete search history.

(56) References Cited

U.S. PATENT DOCUMENTS

| | | |
|---|---|---|
| 5,154,171 A | 10/1992 | Chirife |
| 5,417,715 A | 5/1995 | Noren et al. |
| 5,501,702 A * | 3/1996 | Plicchi et al. ............... 607/20 |
| 5,707,398 A | 1/1998 | Lu |
| 6,070,100 A | 5/2000 | Bakels et al. |
| 6,314,323 B1 | 11/2001 | Ekwall |
| 6,970,742 B2 | 11/2005 | Mann et al. |
| 7,164,947 B2 | 1/2007 | Holmström et al. |
| 2001/0012953 A1 | 8/2001 | Molin et al. |
| 2001/0021864 A1 | 9/2001 | Molin |
| 2003/0204212 A1 | 10/2003 | Burnes et al. |
| 2003/0216657 A1 | 11/2003 | Holmström et al. |
| 2005/0215914 A1 | 9/2005 | Bornzin et al. |
| 2005/0256422 A1 * | 11/2005 | Wik .......................... 600/547 |
| 2006/0149155 A1 | 7/2006 | Hedberg |
| 2006/0184060 A1 * | 8/2006 | Belalcazar et al. ......... 600/547 |
| 2006/0206157 A1 | 9/2006 | Hoijer |
| 2006/0235325 A1 | 10/2006 | Holmström et al. |
| 2006/0271117 A1 | 11/2006 | Burnes et al. |
| 2007/0055170 A1 * | 3/2007 | Lippert et al. ............ 600/547 |
| 2007/0129765 A1 * | 6/2007 | Gilkerson et al. ........... 607/18 |

* cited by examiner

*Primary Examiner* — Carl H Layno
*Assistant Examiner* — Erica Lee

(57) ABSTRACT

In an implantable heart monitoring device and a monitoring method, an impedance is measured across at least part of an atrium, such that variation of the impedance is related to the volume change of the atrium. Values are stored at different occasions that indicate the rate of change of the measured impedance. The stored values are determined such that, when the device is used in a living being, the variation of the stored values will be related to the variation of the speed with which the atrium is filled with blood during the atrial diastole.

11 Claims, 3 Drawing Sheets

IMPLANTABLE HEART MONITORING DEVICE, SYSTEM AND METHOD

BACKGROUND OF THE INVENTION

1. Field of the Invention

The present invention relates to an implantable heart monitoring device, with which it is possible to monitor the heart condition. The invention also concerns a corresponding system and method.

2. Description of the Prior Art

Several different devices for monitoring the performance of a heart are known. Often these devices are also able to deliver stimulation pulses to the heart. The devices are often able to sense the electrical activity in the heart. It is also known to determine an impedance value measured between different electrodes positioned in or at the heart. It is also known to sense other physiological parameters, such as pressure, oxygen level etc.

U.S. Pat. No. 5,154,171 describes the sensing of impedance values in order to control the pacing rate.

U.S. Pat. No. 6,070,100 describes that electrodes may be positioned in or at both the left and the right atria as well as in or at the left and the right ventricles. The document describes the possibility of sensing the impedance between different electrodes. The sensed impedance values may be used to improve the cardiac output.

United States Patent Application Publication No. 2001/0012953 describes bi-ventricular pacing. An impedance may be measured between electrodes on the right and the left sides of the heart. The variation of the impedance with time is detected. The detected impedance variation may be used in order to synchronise the contraction of the ventricles.

United States Patent Application No. 2001/0021864 describes different manners of using the proximal and distal electrodes of different leads in order to inject a current and to measure an impedance. The measured impedance value may be used in order to maximise the cardiac flow.

U.S. Pat. No. 6,314,323 describes a heart stimulator in which the cardiac output is determined by measuring the systolic pressure.

It is also known to communicate with an implanted heart monitoring/stimulating device in a wireless manner, i.e. with the use of so-called telemetry. This can be done by inductive communication or via radio waves. With the help of telemetry it is thus for example possible to obtain information about the status of an implanted device. It is also known to input new information into the device with the help of such telemetry.

For different severe cardiac conditions it may be important to monitor the status of the heart, for instance in order to follow the progress of a heart disease, for example in order to be able to carry out a suitable treatment of the patient. One such heart condition is congestive heart failure (CHF). This is a condition in which the heart's function as a pump to deliver oxygen rich blood to the body is inadequate to meet the body's needs.

Another concept used in this field is pre-load. Pre-load can be defined as the initial stretching of the cardiac myocytes prior to contraction. The concept of pre-load can be applied to either the ventricles or atria. Regardless of the chamber, the pre-load is related to the chamber volume just prior to contraction.

SUMMARY OF THE INVENTION

One object of the present invention is to provide an implantable heart monitoring device with which it is possible to monitor the status of the heart of a patient who suffers from a heart deficiency, such as CHF. A further object is to provide such a device with which it is possible to detect changes in the heart condition at an early stage. Another object is to provide such a device, which with quite simple means makes it possible to monitor the status of the heart condition of a patient who suffers from such heart deficiencies.

The above objects are achieved in accordance with the present invention by an implantable heart monitoring device and system, and a method, wherein an impedance is measured in vivo across a portion of the heart that includes at least a part of an atrium of the heart, and such that the variation of the impedance is related to volume change of the atrium. Further in accordance with the device, system and method, a control circuit is configured to operate in time cycles that correspond to heart cycles of the heart and to, at a first occasion (A) monitor how the measured impedance varies during at least a portion of a time cycle, and (B) determine a value that indicates the rate of change of the measured impedance during at least a part of this portion of the time cycle, and to store that value in a memory. The control circuit is further configured to, at a number of further occasions, (C) repeat (A) and (B) so that, at each of the further occasions, a new determined value, that indicates the rate of change of the measured impedance during the part of the time cycle, is stored in the memory. The values stored in the memory thus represent a record of the variation of the speed with which the atrium is filled with blood during atrial diastole.

When the heart condition becomes worse, the heart will not be able to pump away the returning blood to a sufficient degree, which among other things may result in pulmonary congestion. This will most likely have as a consequence that the (atrial) pre-load as well as the end (atrial) diastolic volume increase. Because of the higher pre-load and the larger end atrial diastolic volume, the atrial walls will be likely to be under more tension and also dilated to a certain extent. Furthermore, more blood will hereby remain in the atrium after the atrial systole (i.e. the atrium will have a higher residual volume). These conditions will have as a consequence that, during the atrial diastole, the atrium will be filled more slowly with new blood.

The rate of change of the measured impedance, in particular when the impedance decreases, is an indication of how fast the atrium in question is being filled with blood during the atrial diastole. With the present invention it is thus possible to monitor the status of the heart by monitoring the mentioned impedance. A worsening of the heart condition is likely to be first noticeable in the atrium. Consequently, with the present invention such a worsening of the heart condition can be detected at an early stage. Moreover, since impedance measurement can easily be provided by an implantable heart monitoring device (for example an implantable cardiac rhythm management device), the invention can be implemented in a quite simple manner.

Preferably, the control circuit is configured to measure the impedance with suitable electrode surfaces such that, when the device is used in a living being, it is the impedance over the left atrium that will be monitored. When the left atrium is monitored, a particularly relevant indication of the progress of the heart condition is obtained.

It should also be noted that preferably, at each occasion, it is the rate of change during the same part of the respective time cycle that is determined.

According to an embodiment of the device according to the invention, the control circuit is configured such that said rate of change of the measured impedance is the rate of change when the impedance decreases. Since the impedance across the atrium decreases when the atrium is being filed with blood, this decreasing impedance is of course a particularly relevant indication of the filling phase of the atrium.

The stored value may be the absolute of the rate of change (i.e. when the impedance decreases, and the rate of change therefore is negative, the stored value may be the rate of change multiplied by −1).

The stored value may be for example the maximum absolute value of the derivative of the impedance as a function of time when the impedance decreases, i.e. the maximum of $$\left|\frac{dZ}{dt}\right|.$$

Another alternative is for example to form the value as:

$$\left|\frac{Z_{max} - Z_{min}}{t}\right|,$$

where $Z_{max}$ is the maximum value of the impedance, preferably the maximum following immediately after a detected QRS, $Z_{min}$ is the subsequent minimum value of the impedance and t is the time between $Z_{max}$ and $Z_{min}$. It is of course not necessary to consider the absolute value of the first derivative. Instead, the minimum of the derivative of the impedance (when it decreases) can be the value that is stored.

Preferably, the control circuit includes cardiac sensing and/or pacing circuits for enabling sensing of cardiac events of one or more atria or ventricles of the heart and/or for pacing one or more atria or ventricles. Such circuits are advantageous, since the heart can thereby be sensed and/or paced.

According to a further embodiment of the device, the control circuit is configured to be able to detect a QRS in a signal sensed from the heart and to determine whether the impedance signal decreases within a short time interval after the detected QRS, such that a major dip in the sensed impedance takes place after the detected QRS, such that the measured impedance is likely to actually reflect the inverse of the amount of blood in an atrium.

For example, the onset of the QRS may be detected (the QRS is the ventricular depolarisation seen in the sensed signal). If the impedance decreases substantially directly after the (onset of the) QRS, this is an indication of the fact that it is actually an atrium that is monitored. If, on the other hand, the impedance increases substantially directly after the (onset of the) QRS, this is an indication of the fact that it is more likely that it is a ventricle that is monitored. If the latter is the case, the control circuit can be configured not to use the measured impedance, since it does not reflect an atrium, which it is intended to monitor.

It should be noted that the detection of the occurrence of the QRS in relation to the measured impedance is just one advantageous manner of determining that the measured impedance actually reflects when the atrium is being filled with blood. Also other alternatives are possible. The idea is that by determining in which part of the heart cycle the impedance is measured, and by observing that the measured impedance actually decreases as expected during the relevant part of the heart cycle, it can be determined that it is very likely that it is an atrium that is being monitored. This can however be done in other manners than by detecting the QRS. Instead, or additionally, other indications of the different parts of the heart cycle can be used. It is for example possible to monitor the pressure in a heart chamber or the movement of a heart wall in order to determine in which part of the heart cycle the impedance is being measured. It is also possible to detect the operation of the ventricles in different manners in order to determine the part of the heart cycle. For example, it is possible to monitor the impedance across at least one ventricle in order to detect when the ventricular systole is taking place. If another measured impedance (the impedance that is supposed to relate to the atrium in question) actually decreases as expected during the ventricular systole, this is an indication of the fact that it is actually the atrium that is being monitored with the latter impedance measurement.

According to a further embodiment, the control circuit is configured to select said occasions such that the living being is likely to be in a similar physical and/or psychological state at the different occasions. An accurate indication of the progress of the heart condition can be obtained if it is ensured that the patient is in a similar state at the different occasions.

According to a further embodiment, the control circuit is configured to be able to determine the physical and/or psychological state by one or more of the following:

i) a physical activity sensor in the implantable heart monitoring device, ii) the heart rate sensed or paced with the use of the implantable heart monitoring device, iii) a sensed breathing of the living being, iv) a sensed posture of the living being, for example whether the living being is standing up or laying down, v) the time of day.

With such measures, the state of the patient can be determined automatically.

According to a further embodiment, the control circuit is configured such that at each of said occasions, steps A and B are carried out a number of times and such that from these number of times a representative value that indicates said rate of change at the occasion in question is formed, and wherein it is this representative value that is stored in the memory at the occasion in question. By determining the rate of change of the measured impedance a plurality of times, a more accurate representative value can be obtained.

According to an embodiment, said plurality of times takes place within 1 hour, preferably within 5 minutes, more preferred within 1 minute. Thereby an accurate representative value can be formed that represents the rate of change of the measured impedance at the occasion in question.

The representative value that is stored may for example be the mean value of 30 measurements, performed within two minutes. According to one option, values that deviate too much from predefined normal values may be ignored.

According to another embodiment, the control circuit is configured to communicate with three or more electrode surfaces and also configured to be able to carry out a procedure that involves testing different combinations of electrode surfaces used for injecting a current into the living being in question and/or testing different combinations of electrode surfaces used for sensing the voltage there between, in order to determine an optimal combination of electrode surfaces with which an optimal impedance measurement for indicating the volume change of the atrium is obtained. By this measure, the impedance measurement may be improved, since an optimal combination of electrode surfaces is used.

According to a further embodiment, the control circuit is configured to determine said optimal combination of electrode surfaces based on one or more of the following criteria:

the strength of the detected signal, the ratio signal/noise of the detected signal, the fact that the impedance signal decreases in such a part of the time cycle that the decreasing signal is likely to represent the filling of the atrium with blood.

In this way, the optimal combination of electrode surfaces can be determined in a quite straight forward manner. In order to determine whether the last mentioned criteria is fulfilled, the control circuit can be arranged at explained above, i.e. for example in order to determine whether the decreasing impedance follows directly after a detected QRS.

According to a further embodiment, the control circuit is configured such that said different occasions are distributed over at least several days, preferably over several weeks, or months, such that the variation of the stored values represents the variation in the detected rate of change of the measured impedance during a longer period. The long term change of the heart condition thus can be monitored.

According to a further embodiment, the control circuit is configured to create a warning message if the stored values change more than a predetermined amount over a predefined time period.

The warning message may for example be created if the stored (absolute) value that represents the rate of change of the impedance has decreased more that 20% since the first (absolute) value was stored, i.e. compared to the (absolute) value stored at the first occasion. According to another example, the warning message may be created if the stored (absolute) value that represents the rate of change of the impedance has decreased more that 10% within two days. The warning message may for example be that a warning is stored in the memory in order to alert a physician at the next check-up. Another possibility is that the warning message directly alerts the patient carrying the device.

According to another embodiment, the control circuit is configured such that a plurality of said occasions, preferably at least 10 occasions, takes place during 24 hours such that the variation of the stored values represents the variation in the detected rate of change of the measured impedance during a 24 hour period.

Moreover, the control circuit may be configured to carry out this procedure at a plurality of different days and to determine, for each day, the variation in the detected rate of change of the measured impedance during each 24 hour period, and to also determine how the determined variation changes from day to day.

According to an embodiment, the control circuit is configured to create a warning message if the change, from day to day, of the determined variation, in the detected rate of change of the measured impedance during a 24 hour period, fulfils a predetermined criteria.

The criteria may for example be that the determined variation, in the detected rate of change of the measured impedance during a 24 hour period, has decreased more than 20% since the previous determined variation in the detected rate of change of the measured impedance during a 24 hour period. The rate of change is likely to vary to a certain degree during a day (during a 24 hour period). If this is not the case, this may be an indication of the fact that the heart condition has become worse.

According to a further aspect, the invention provides an implantable heart monitoring system, comprising an implantable heart monitoring device according to any one of the preceding embodiments and at least two of the electrode surfaces adapted to be positioned in a heart or in relation to a heart of a living being, wherein the control circuit is set up to communicate with said electrode surfaces.

Although the control circuit could communicate with the electrode surfaces in a wireless manner, the implantable heart monitoring system preferably also comprises leads, which carry the electrode surfaces and which are adapted to be physically connected to the implantable heart monitoring device.

With such an implantable heart monitoring system, advantages corresponding to those described in connection with the implantable heart monitoring device are achieved.

According to a further aspect, the invention provides a method of monitoring a heart that proceeds as described in connection with the operation of the implantable heart monitoring device. Such a method brings about advantages corresponding to those described in connection with the implantable heart monitoring device.

In analogy with the operation of the described device, also in the method, in order to monitor when the atrium is being filled with blood, it is the rate of change of the measured impedance when the impedance decreases that is considered. Also in the method it is preferably the impedance over the left atrium that is measured, such that it is the filling of the left atrium with blood that is being monitored.

DESCRIPTION OF THE PREFERRED EMBODIMENTS

Figure 1:
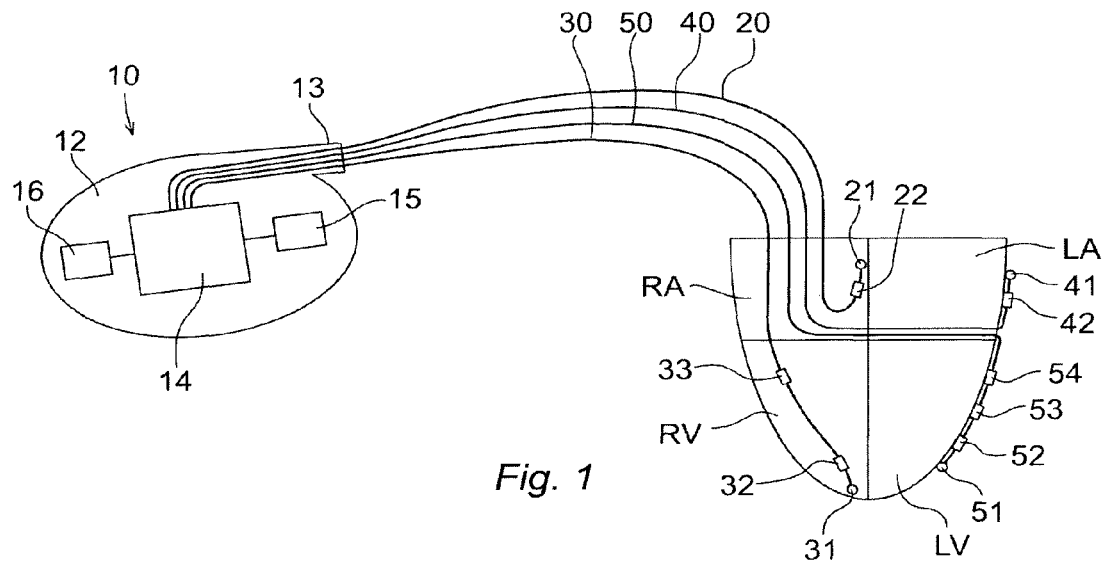
FIG. 1 shows schematically an implantable heart monitoring device with leads and electrodes positioned in or in relation to a heart.

FIG. 1 shows schematically an embodiment of an implantable heart monitoring device 10 according to the invention. The device 10 has a casing 12, which may also function as an electrode surface in connection with for example impedance measurements. The device 10 has a control unit 14, which controls the operation of the device 10. The device 10 also comprises a memory 15 connected to the control circuit 14. Furthermore, the device 10 has an activity sensor 16 for sensing how physically active the living being that carries the device 10 is. The sensor 16 is connected to the control circuit 14.

The device 10 has a connector portion 13, via which the device 10 can be connected to different leads 20, 30, 40, 50. The leads 20, 30, 40, 50 are provided with electrode surfaces 21, 22, 31, 32, 41, 42, 51, 52, 53, 54. The electrode surfaces 21, 31, 41, 51 are so-called tip electrodes, while the other electrode surfaces 22, 32, 42, 52, 53, 54 are so-called ring electrodes.

The device 10 together with the leads 20, 30, 40, 50 and the mentioned electrode surfaces together constitute an embodiment of a system according to the invention.

It should be noted that the device (and the system) may have many more components and functions which are normal for a heart monitoring and pacing device.

The implantable heart monitoring device 10 is preferably also set up to be able to sense the electrical activity of the heart and to pace different heart chambers. In the shown embodiment, the lead 20 has been introduced into the right atrium RA such that the electrode surfaces 21, 22 are positioned in this atrium. The lead 30 has been introduced into the heart such that the electrode surfaces 31, 32 are positioned in the right ventricle RV. This lead 30 also has a pressure sensor 33 for sensing the pressure in the right ventricle RV. The electrode surfaces 21, 22 can thus be used to sense and pace the right atrium RA and the electrode surfaces 31, 32 can be used to sense and pace the right ventricle RV.

The lead 40 has been introduced via the right atrium RA and the coronary sinus such that the electrode surfaces 41, 42 are positioned in a vein next to the left atrium LA. Similarly, the lead 50 has been introduced via the right atrium RA and the coronary sinus such that the electrode surfaces 51-54 are positioned in a vein next to the left ventricle LV. The different electrode surfaces 41, 42, 51-54 can thus be used to pace and sense the left atrium LA and the left ventricle LV in a manner known to a person skilled in the art. In this example, the lead 50 has four different electrode surfaces 51-54 which make it possible to choose which electrode surfaces are to be used for sensing and pacing.

It is also well-known to a person skilled in the art that different electrode surfaces can be used for injecting a current and for sensing a voltage in order to measure an impedance across at least a portion of the heart. Also the casing 12 can be used for this purpose.

Figure 2:
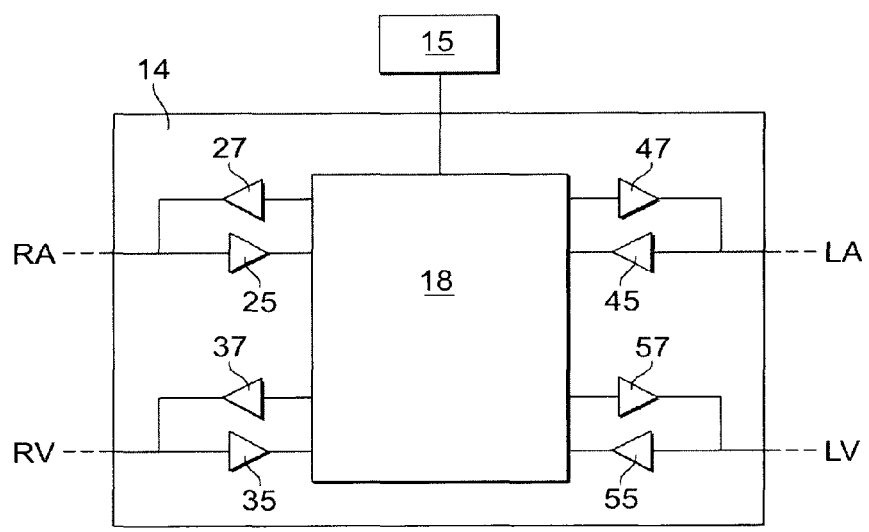
FIG. 2 shows schematically a control circuit and a memory which are comprised in the heart monitoring device.

FIG. 2 shows schematically in particular the control circuit 14 in some more detail. The control unit 14 has a control circuit 18 that controls the overall operation of the control unit 14. The control circuit 18 is connected to be above mentioned memory 15. Furthermore, as is known to those skilled in the art, the control unit 14 may comprise a sensing circuit 25 and a pacing circuit 27, which circuits are adapted to be connected to the lead 20 in order to pace and sense the right atrium RA. Moreover, a sensing circuit 35 and a pacing circuit 37 are adapted to be connected to the lead 30 in order to sense and pace the right ventricle RV. Furthermore, a sensing circuit 45 and a pacing circuit 47 are adapted to be connected to the lead 40 in order to sense and pace the left atrium LA. A sensing circuit 55 and a pacing circuit 57 are adapted to be connected to the lead 50 in order to sense and pace the left ventricle LV. The different sensing and pacing circuits are of course also connected to the control portion 18. Although not shown, the control unit 14 may be adapted to be connected to different ones of the electrode surfaces 51-54 arranged on the lead 50 in order to make it possible to select which of the electrode surfaces 51-54 that are to be used. Of course, also the other leads 20, 30 and 40 may be provided with more or less than two electrode surfaces.

The control unit 14 is also configured to communicate with a number of electrode surfaces 12, 21, 22, 31, 32, 41, 42, 51, 52, 53, 54 and to measure an impedance with the help of at least two such electrode surfaces 12, 21, 22, 31, 32, 41, 42, 51, 52, 53, 54. The impedance indicates preferably the impedance across a portion of the heart that includes at least a part of the left atrium LA. How to measure such an impedance is known to a person skilled in the art, for example from some of the above-mentioned documents. For example, the control unit 14 can be configured to inject a current between the electrode surfaces 22 and 52 and to measure a voltage between the same electrode surfaces 22, 52. However, many other combinations of electrode surfaces can be used for the impedance measurement, and different electrode surfaces may be used for injecting a current and for measuring a voltage. However, the control circuit 14 is preferably set up such that the variation of the measured impedance is related to the volume change of an atrium, preferably the left atrium LA.

The control unit 14 is configured to operate in time cycles corresponding to heart cycles. This is normal for an implantable heart monitoring or pacing device. The control unit 14 is configured to carry out the following steps: at a first occasion, A) monitor how the measured impedance varies during at least a portion of a time cycle, and B) determine a value that indicates the rate of change of the measured impedance during at least a part of said portion of the time cycle, and store the value in the memory 15, and at a number of further occasions, C) repeat steps A and B, such that at the different occasions a new determined value, that indicates the rate of change of the measured impedance during said part of the time cycle, is stored in the memory 15.

The control unit 14 is configured such that the values that are stored in the memory 15 have been determined such that, when the device 10 is actually used in a living being, the variation of the stored values will be related to the variation of the speed with which the atrium is filled with blood during the atrial diastole.

The control unit 14 is configured such that the rate of change of the measured impedance is the rate of change when the impedance decreases. This means that the impedance is measured when the atrium LA is being filled with blood.

In order to make sure that the measured impedance actually reflects the amount of blood in the atrium, the control unit 14 is configured to carry out the impedance measurement during a certain portion of the heart cycle (i.e. a portion of the mentioned time cycle with which the device operates). This can for example be done by detecting a QRS in the signal sensed from the heart. The control unit 14 is configured to determine whether the measured impedance decreases within a short time interval after the detected QRS, such that a major dip in the sensed impedance takes place after the detected QRS. This means that the measured impedance is likely to actually reflect the inverse of the amount of blood in an atrium.

Figure 3:
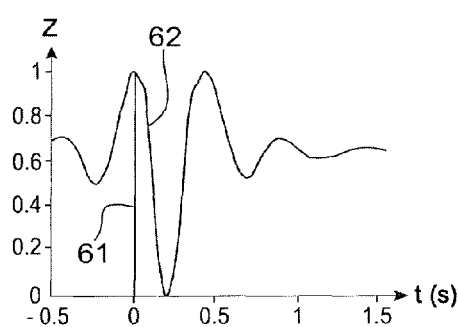
FIG. 3-5 shows examples of measured impedance as a function of time.
Figure 4:
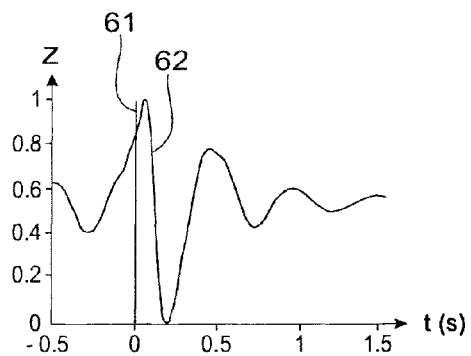
Figure 5:
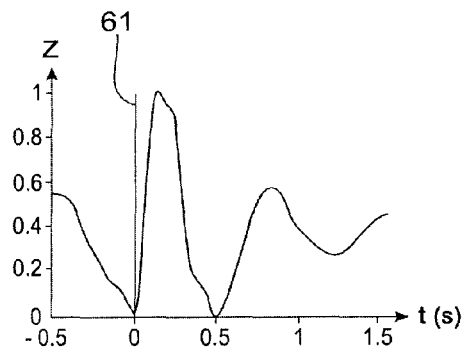

FIG. 3-5 illustrate examples of how the measured impedance Z (in fact a normalised value that indicates how the impedance varies) as a function of time t in seconds. The time 0 in the figures is the time when the QRS is sensed. The QRS is symbolised by the line 61. As can be seen in FIG. 3 and FIG. 4, the measured impedance signal decreases rapidly directly, or shortly, after the QRS 61. This is an indication of the fact that the measured impedance actually reflects the amount of blood in the atrium.

In FIG. 5, on the other hand, the impedance increases rapidly directly after the sensed QRS 61. This is an indication of the fact that in FIG. 5, the measured impedance is more likely to reflect a ventricle than an atrium.

This may be caused by the fact that the electrode surface (for example 52), which is one of the electrode surfaces used for the impedance measurement, is positioned so far down along the left ventricle LV that the measured impedance mainly reflects the left ventricle LV.

The control unit 14 is preferably configured to test different combinations of electrode surfaces 12, 21, 22, 31, 32, 41, 42, 51, 52, 53, 54 used for injecting a current and for measuring a voltage in order to determine an optimal combination of electrode surfaces 12, 21, 22, 31, 32, 41, 42, 51, 52, 53, 54 with which an optimal impedance measurement for indicating the volume change of the atrium LA is obtained. The control circuit 14 may hereby be configured to determine the optimal combination of electrode surfaces 12, 21, 22, 31, 32, 41, 42, 51, 52, 53, 54 based on one or more of the following criteria:

the strength of the detected signal, the ratio signal/noise of the detected signal, the fact that the impedance signal decreases in such a part of the time cycle that the decreasing signal is likely to represent the filling of the atrium LA with blood.

Thus it can be determined that it is actually an atrium, in particular the left atrium LA, that is being monitored. Furthermore, an optimal signal reflecting the impedance can thereby be obtained.

The value that at the different occasions is stored in the memory 15 reflects the rate of change of the impedance at the major slope 62 of the signal when the impedance decreases, i.e. the slope 62 reflects when the atrium LA is being filled with blood. As mentioned above, the value that is stored may for example be that maximum of the absolute of the first derivative dZ/dt when the impedance decreases according to the slope 62.

In order to get a more accurate value that represents the rate of change of the impedance, the control unit 14 may be configured such that at each occasion the steps A and B are carried out a plurality of times and such that from this plurality of times a representative value that indicates the rate of change at the occasion in question is formed, and wherein it is this representative value that is stored in the memory 15. The stored value may for example be the mean value of 30 measurements, performed within two minutes, of the rate of change of the measured impedance.

Preferably, the control unit 14 is configured to select the different occasions such that the living being is likely to be in a similar physical and/or psychological state at the different occasions. This can be done by the fact that the control circuit 14 is configured to be able to determine the physical and/or psychological state by means of one or more of the following:

i) a physical activity sensor 16 which is comprised in the implantable heart monitoring device 10, ii) the heart rate sensed or paced with the help of the implantable heart monitoring device 10, iii) a sensed breathing of the living being, iv) a sensed posture of the living being, for example whether the living being is standing up or laying down, v) the time of day.

It is known in the art how these different matters can be sensed or detected.

The control unit 14 is configured such that the different occasions are distributed over several days such that the variation of the stored values represents the variation in the detected rate of change during a longer period.

Figure 6:
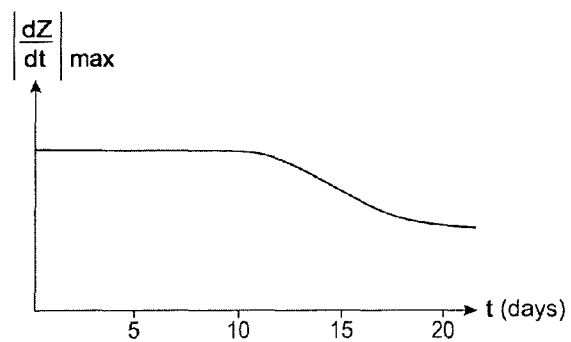
FIG. 6 shows schematically an example of how the rate of change of the measured impedance may vary over time.

FIG. 6 illustrates an example of how the stored values (that represent the mentioned maximum of the absolute of dZ/dt at the occasion in question) vary over a number of days. In FIG. 6 it can be seen that the stored values decrease substantially after about 12 days. This is an indication of the fact that the heart condition became worse after about 12 days.

The control unit 14 can be configured to create a warning message if the stored values change more than a predetermined amount over a predefined time period. For example, a warning message may be created if the stored value has decreased more than 20% since the first value was stored (i.e. if the actual last value stored is less than 80% of the first stored value).

The control unit 14 may also be configured such that for example 24 of the occasions take place during a 24 hour period such that the variation of the stored values represents the variation in the detected rate of change of the measured impedance during a 24 hour period. The control unit 14 can be configured to for each day also store a value that represents the variation in the detected rate of change of the measured impedance during each 24 hour period, and to determine how the determined variation changes from day to day. A warning message may for example be created if the change, from day to day, of the determined variation, in the detected rate of change of the measured impedance during a 24 hour period, has decreased more than 20% since the previous determined variation in the detected rate of change of the measured impedance during a 24 hour period.

Figure 7:
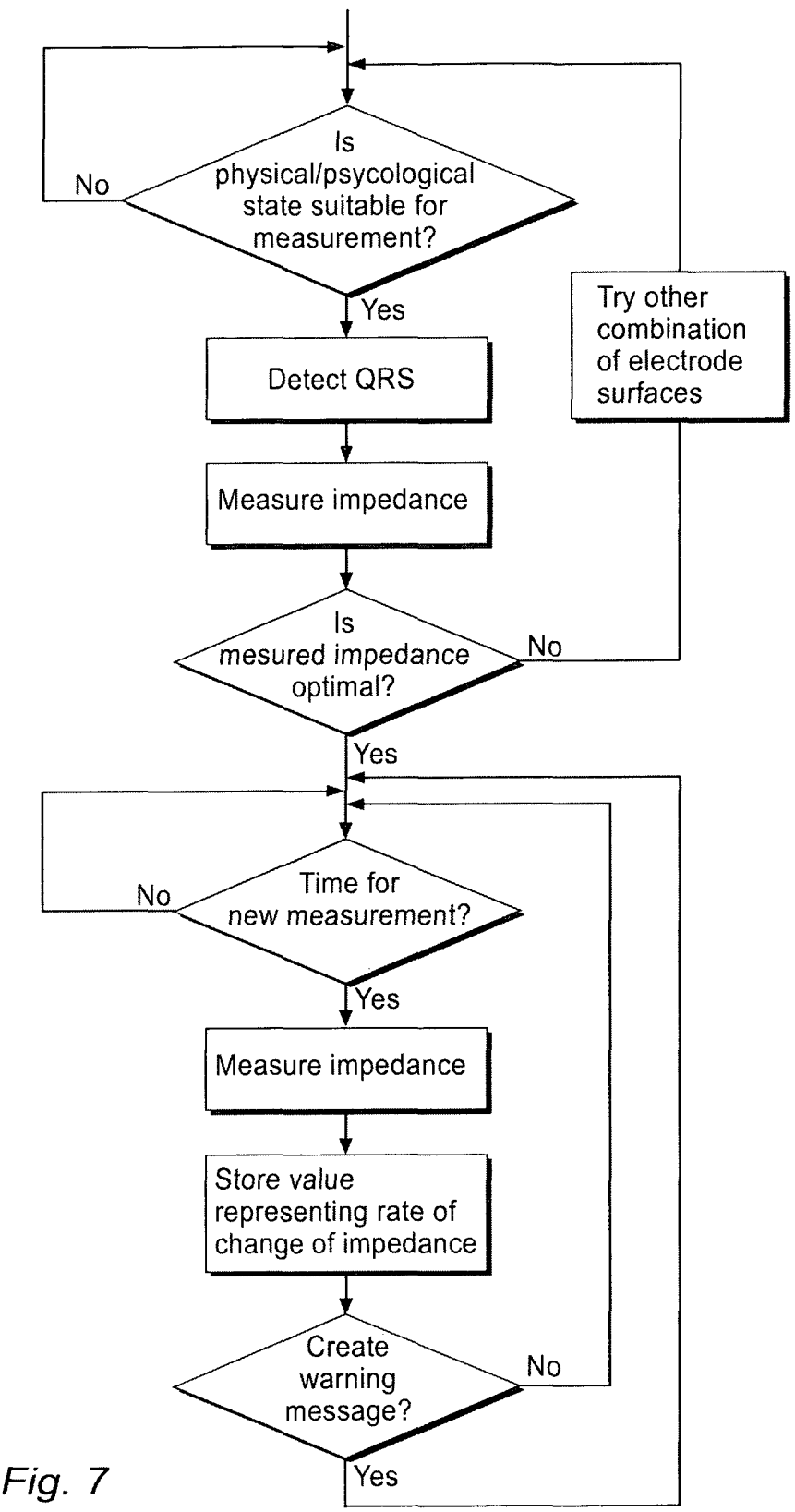
FIG. 7 is a schematic flow chart illustrating a method according to the invention.

FIG. 7 shows a schematic flow chart illustrating a manner of carrying out a method according to the invention.

In a first step it can be determined, in the same manner as explained above, whether the patient is in a physical/psychological state that is suitable for carrying out the impedance measurement. If this is not the case, the measurement is not carried out at the present moment. If, however, the state of the patient is suitable for measurement, then a QRS is detected. The impedance is measured as explained above within a short time interval after the detected QRS.

In the next step, it is determined whether the measured impedance is optimal. This can be done as explained above. Among other things, it is decided whether the impedance actually decreases as expected if the impedance represents the amount of blood in the left atrium LA. Furthermore, signal/noise etc may be detected in order to decide whether the measured impedance is optimal. If this is not the case, another combination of electrode surfaces is tested for injecting a current and for measuring a voltage. When an optimal measured impedance (or a sufficiently reliable impedance measurement) is obtained, a suitable electrode combination has thus been decided. The method then continues with the actual measurements that are to be monitored and stored.

If it is time for a new measurement (a new occasion), then (although not shown in the figure) it is first determined whether the patient is in a suitable state for measurement, and, if this is the case, the impedance is measured by A) monitoring how the measured impedance varies during the specific portion of the heart cycle and by B) determining a value that represents the rate of change of the measured impedance during at least a part (the slope 62 in FIGS. 3 and 4) of the portion of the heart cycle. In order to determine that it is the correct portion of the heart cycle that is considered, it is possible to detect for example the QRS as explained above.

A value that represents the rate of change of the impedance during said part of the heart cycle is stored in the memory 15. Preferably, at each occasion, the steps A and B are carried out a plurality of times such that a representative value that indicates the rate of change at the occasion in question is stored in the memory.

In the next step, it is decided whether a warning message should be created. The criteria for creating a warning message may be analogous to those described above. A warning message may for example be created if the recently stored value that represents the rate of change of the impedance is more than 20% lower than the first value that was stored.

When it is time for a new measurement, the described procedure is performed again. The procedure may be performed for example once a day in order to monitor the variation in the detected rate of change of the measured impedance during a longer period. However, it is also possible to perform the procedure for example every hour such that also the variation of the stored values represents the variation in the detected rate of change of the measured impedance during a 24 hour period. This can be done at a plurality of different days such that it is determined how the determined variation changes from day to day.

With the present invention it is thus possible to monitor the heart condition and to discover, at an early stage, if the heart condition becomes worse. The stored values and the warning messages may be communicated to a physician, for example with the help of so-called telemetry or in other manners. It is also possible to arrange the device such that the device automatically carries out a measure if the heart condition becomes worse. For example, the device may in that case change a pacing routine in order to improve the function of the heart. The device may also be arranged to automatically deliver a suitable pharmaceutical drug to the patient in question in response to the detected heart condition.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable heart monitoring system comprising:
    a control unit comprising a control circuit; a memory in communication with said control circuit;
    a plurality of electrode surfaces adapted for positioning to measure an impedance across at least a part of an atrium of the heart to generate an impedance signal that varies as a function of a change in volume of said atrium;
    cardiac sensing circuitry in communication with at least some of said electrode surfaces to sense cardiac events in at least one chamber of the heart;
    said control circuit being configured to determine a first value indicating the rate of change of the measured impedance signal during at least a portion of a first cardiac cycle, and to store the first value in said memory; and said control circuit being configured to determine a second value indicating the rate of change of the measured impedance signal during at least a portion of a second cardiac cycle and to store the second value in said memory, to produce, in said memory, a record of stored values having a variation that is related to variation of a speed with which the atrium is filled with blood during atrial diastole, wherein said control circuit is configured to determine whether said impedance signal decreases within a time interval following detection of a QRS signal by the cardiac sensing circuitry to determine whether the measured impedance indicates an inverse of an amount of blood in the atrium.

2. An implantable heart monitoring system as claimed in claim 1 wherein said control circuit is configured to determine said rate of change of said measured impedance as a rate of change when said measured impedance decreases.

3. An implantable heart monitoring system as claimed in claim 1 comprising a state detector in communication with said control circuit that supplies information to said control circuit selected from the group consisting of physical activity of the subject, the heart rate of the subject, respiration of the subject, posture of the subject, and time of day.

4. An implantable heart monitoring system as claimed in claim 1 wherein said control circuit is configured to communicate with at least three of said plurality of electrode surfaces to test different combinations of said at least three plurality of electrode surfaces for supplying current thereto or for detecting a voltage there across to identify an optimal combination of said at least three plurality of electrode surfaces for making said impedance measurement to indicate said volume change of said atrium.

5. An implantable heart monitoring system as claimed in claim 4 wherein said control circuit is configured to determine said optimal combination of said at least three plurality of electrode surfaces from at least one criterion selected from the group consisting of a strength of a detected signal, a signal-to-noise ratio of a detected signal, and occurrence of a decrease in the detected signal in a part of said time cycle that is likely to represent filling of the atrium with blood.

6. An implantable heart monitoring system as claimed in claim 1 wherein said control circuit is configured to emit a humanly perceptible warning when the values stored in said memory change more than a predetermined amount within a predetermined time period.

7. An implantable heart monitoring system as claimed in claim 1 wherein said control circuit is configured to emit a humanly perceptible warning when the rate of change of said measured impedance from one of said periods to a next of said periods satisfies at least one predetermined criterion.

8. An implantable heart monitoring device comprising:
    cardiac sensing circuitry in communication with at least some of said electrode surfaces to sense cardiac events in at least one chamber of the heart;
    a control unit comprising a control circuit; a memory in communication with said control circuit; said control circuit being configured to determine a first value indicating the rate of change of a measured impedance during at least part of a first cardiac cycle, and to store said first value in said memory; and said control circuit being configured to determine a second value indicating the rate of change of the measured impedance during at least part of a second cardiac cycle and to store said second value in said memory, to produce, in said memory, a record of stored values having a variation that is related to variation of a speed with which the atrium is filled with blood during atrial diastole, wherein said control circuit is configured to determine whether said impedance decreases within a time interval following detection of a QRS signal by the cardiac sensing circuitry to determine whether the measured impedance indicates an inverse of an amount of blood in the atrium.

9. A heart monitoring method comprising the steps of:
    measuring an impedance across at least a part of an atrium of the heart to generate an impedance signal that varies as a function of a change in volume of said atrium;
    determining a first value indicating the rate of change of the measured impedance signal during at least a portion of a first cardiac cycle;
    storing said first value in memory; and
    determining a second value indicating the rate of change of the measured impedance signal cardiac cycle;
    storing the second value in the memory wherein the first and second stored values provide information related to variation of a speed with which the atrium is filled with blood during atrial diastole; and
    detecting a QRS complex and determining whether said impedance signal decreases within a time interval following said QRS complex to detect whether the measured impedance indicates an inverse of an amount of blood in the atrium.

10. A heart monitoring method as claimed in claim 9 comprising, communicating with at least three electrode surfaces to test different combinations of said at least three electrode surfaces for supplying current thereto or for detecting a voltage there across to identify an optimal combination of said at least three electrode surfaces for making said impedance measurement to indicate said volume change of said atrium.

11. A heart monitoring method as claimed in claim 9 comprising, emitting a humanly perceptible warning when the rate of change of said measured impedance from one of said periods to a next of said periods satisfies at least one predetermined criterion.

* * * * *